United States Patent [19]

Graybill et al.

[11] Patent Number: 5,300,528
[45] Date of Patent: Apr. 5, 1994

[54] USE OF PERFLUOROETHYLDIMETHYL CYCLOHEXANE FOR OXYGEN TRANSPORT

[75] Inventors: John K. Graybill, Macungie, Pa.; Gregory B. George, Largo, Fla.

[73] Assignee: Air Products and Chemicals, Inc., Allentown, Pa.

[21] Appl. No.: 932,520

[22] Filed: Aug. 20, 1992

Related U.S. Application Data

[63] Continuation-in-part of Ser. No. 724,613, Jul. 2, 1991, Pat. No. 5,146,014.

[51] Int. Cl.$^5$ ............................................. A61K 47/06
[52] U.S. Cl. ................................. 514/772; 514/832; 514/833
[58] Field of Search ........................ 514/772, 832, 833

[56] References Cited

U.S. PATENT DOCUMENTS

| | | | |
|---|---|---|---|
| 2,606,212 | 8/1952 | McBee et al. | 260/648 |
| 3,776,857 | 12/1973 | Lindner | 252/308 |
| 3,962,439 | 6/1976 | Yokoyama et al. | 424/248 |
| 4,397,870 | 8/1983 | Sloviter | 424/325 |
| 4,423,077 | 12/1983 | Sloviter | 424/325 |
| 4,443,480 | 4/1984 | Clark, Jr. | 424/352 |
| 4,453,028 | 6/1984 | Lagow | 570/130 |
| 4,497,829 | 2/1985 | Sloviter | 514/672 |
| 4,639,364 | 1/1987 | Hoey | 424/9 |
| 4,686,085 | 8/1987 | Osterholm | 422/45 |
| 4,781,676 | 11/1988 | Schweighardt et al. | 604/21 |
| 4,801,761 | 1/1989 | Bailey et al. | 570/130 |
| 4,838,274 | 6/1989 | Schweighardt et al. | 128/654 |
| 4,859,363 | 8/1989 | Davis et al. | 252/312 |
| 4,866,096 | 9/1989 | Schweighardt | 514/756 |
| 4,895,876 | 1/1990 | Schweighardt et al. | 514/747 |
| 5,068,098 | 11/1991 | Schweighardt et al. | 424/9 |

FOREIGN PATENT DOCUMENTS

| | | |
|---|---|---|
| 0089815 | 9/1983 | European Pat. Off. |
| 0118281 | 9/1984 | European Pat. Off. |
| 0231091 | 8/1987 | European Pat. Off. |
| 20911098 | 7/1982 | United Kingdom |
| 2110204 | 6/1983 | United Kingdom |

OTHER PUBLICATIONS

Reiss, Jean G. "Reassessment of Criteria for the Selection of Perfluorochemicals for Second-Generation Blood Substitutes: Analysis of Structure/Property Relationships." *Artificial Organs* 8(1):44-56, May 1983.

Levine, Edward M. and Alan E. Friedman. "Artificial Blood on the Laboratory Horizon." *Lab World* Oct. 1980: 56.

Bottomley, Paul A. "NMR in Medicine." *Computerized Radioi* 8 (2): 57-77, 1984.

Mattrey, Robert F. "Perfluorocarbon Compounds: Applications in Diagnostic Imaging." SPIE vol. 626 Medicine XIV/PACS IV (1986), 18-23.

Longmaid, H. E. III, et al. "In Vivo $^{19}$F NMR Imaging of Liver, Tumor, and Abscess in Rats." *Investigative Radiology* Mar.-Apr. 1985, 141-45.

Patronas, Nicholas J., et al. "Brain-Tumor Imaging Using Radiopaque Perfluorocarbon." *J. Neurosurg.* May 1983, 650-53.

Mattrey, Robert E., et al. "Perfluorochemicals as U.S. Contrast Agents for Tumor Imaging and Hepatosplenography: Preliminary Clinical Results." *Radiology* 1987; 163:339-43.

Parhmai, Pejman and B. M. Fung. "Fluorine-19 Relaxation Study of Perfluoro Chemicals as Oxygen Carriers." *J. Phys. Chem.* 1983, 87, 1928-31.

(List continued on next page.)

*Primary Examiner*—Frederick E. Waddell
*Assistant Examiner*—William R. A. Jarvis
*Attorney, Agent, or Firm*—Geoffrey L. Chase; James C. Simmons; William F. Marsh

[57] ABSTRACT

Gas transport and bio-inert fluid administration to biological systems methods using a novel composition of matter are disclosed wherein the composition of matter comprises perfluorinated, ethyldimethyl cyclohexane. The compound has unique utilities in vapor phase heating and soldering, oxygen transport for biological fluids and other requirements for an inert, stable fluid.

15 Claims, No Drawings

FOREIGN PATENT DOCUMENTS

Nunnally, R. L., et al. "Fluorine-19 ($^{19}$-F) NMR in Vivo: Potential for Flow and Perfusion Measurements." Proc. of the Second Annual Meeting of the Society of Magnetic Resonance in Medicine. 16–19 Aug. 1983, San Francisco, Calif.: NMR Research, 266.

Reid, R. S., et al. "The Influence of Oxygenation of the $^{19}$F Spin–Lattice Relaxation Rates of Fluosol-DA." *Phys. Med. Biol.* 30 (7) 677–86, 1985.

Wyrwicz, A. M., et al. "Observations of Fluorinated Anesthetics in Rabbit Brain by $^{19}$F NMR." Proc. of the Second Annual Meeting of the Society of Magnetic Resonance in Medicine. 16–19 Aug. 1983, San Francisco, Calif.: NMR Research, 381–82.

Clark, Leland C., Jr., et al. "Perfluorinated Organic Liquids and Emulsions as Biocompatible NMR Imaging Agents for Fluorine-19 and Dissolved Oxygen." *Adv. Exp. Med. Biol.* 180, 1984:835–45.

Lauterbur, P. C. "Image Formation of Induced Local Interactions: Examples Employing Nuclear Magnetic Resonance." *Nature* 16 Mar. 1973: 190–91.

Damadian, Raymond. "Tumor Detection by Nuclear Magnetic Resonance." *Science* 19 Mar. 1971: 1151–153.

Ohyanagi, H. and Y. Saitoh. "Development and Clinical Application of Perfluorochemical Artificial Blood." *Int'l J. of Artificial Organs* 9 (5) 1986: 363–68.

Yamanouchi, Kouichi and Charles Heldebrant. "Perfluorochmeicals As A Blood Substitute." *Chemtech* Jun. 1992: 354–59.

Yokoyama, Kazumasa, et al. "Development of Perfluorochemical (PFC) Emulsion As An Artificial Blood Substitute." *Biomedical Aspects of Fluorine Chemistry.* Ed. Robert Filler and Yoshiro Kobayashi. Japan: Kodansha, 1982. 191–211.

Clark, Leland C., Jr., and Robert Moore. "Basic and Experimental Aspects of Oxygen Transport by Highly Fluorinated Organic Compounds." *Biomedical Aspects of Fluorine Chemistry.* Ed. Robert Filler and Yoshiro Kobayashi. Japan: Kodansha, 1982. 213–226.

USE OF PERFLUOROETHYLDIMETHYL CYCLOHEXANE FOR OXYGEN TRANSPORT

This application is a continuation-in-part of application Ser. No. 07/724,613, filed Jul. 2, 1991 now U.S. Pat. No. 5,146,014.

FIELD OF THE INVENTION

The present invention is directed to the use of a novel composition comprising perfluoroethyldimethyl cyclohexane for oxygen transport and to administer a bioinert fluid to a biological system. More specifically, the present invention is directed to perfluoro-1-ethyl-2,4-dimethyl cyclohexane for the transport of oxygen in biological systems.

BACKGROUND OF THE PRIOR ART

Various prior art compounds have been synthesized and more specifically fluorinated to provide at least partially fluorinated organic compounds having a high degree of heat stability. For instance, in U.S. Pat. No. 2,606,212, compounds are disclosed which are derivatives of cyclohexane having full substitution of any hydrogen with fluorine and with various alkyl radicals on the cyclohexane ring. For example, perfluoro-1,2,4-trimethyl cyclohexane is disclosed in the patent, and perfluoro-1, 3-diethyl-5-methyl cyclohexane is disclosed in the patent. However, compounds such as these have not satisfied particular needs for an inert fluid having a precise boiling point, vapor pressure and gas transport capabilities as is provided by the use of the present invention, which is set forth below.

Yamanouchi et al in "Perfluorochemicals as a Blood Substitute", CHEMTECH, June 1992, p. 354–358, describe the general applicability of known fluorochemicals as blood substitutes.

BRIEF SUMMARY OF THE INVENTION

The present invention is a method of transporting gases in a fluid system, the improvement comprising using as the gas transport agent a perfluorinated compound having the following structure wherein the ring carbons are fully fluorinated:

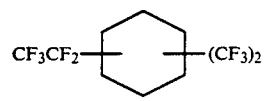

Preferably, the method uses a compound having the following structure:

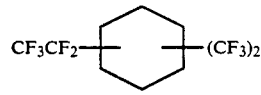

Preferably, the method uses a compound having the following structure:

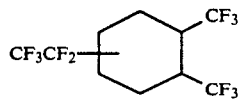

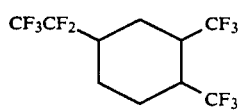

Alternatively, the method uses a compound having the following structure:

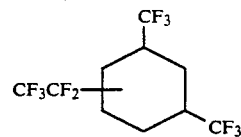

Alternatively, the method uses a compound having the following structure:

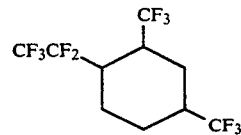

Further alternatively, the method uses a compound having the following structure:

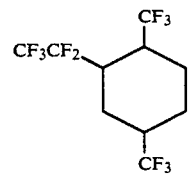

Preferably the gas is oxygen.

More specifically the present invention is a method of transporting oxygen gas in a fluid system selected from the group consisting of resusitative blood replacement fluid, radiotherapy fluid for hypoxic tumor therapy, therapeutic fluid for angioplasty, organ preservation fluid for organ transplants, fluid for liquid lung breathing therapy, therapeutic lavage for cystic fibrosis, and cell culture media, using as the gas transport agent a perfluorinated compound of the formula:

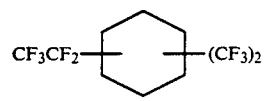

Preferably, the perfluorinated compound is in an aqueous emulsion.

Alternatively, the present invention is a method of administering a bio-inert fluid to a biological system, the improvement comprising a biocompatible fluid containing perfluoroethyldimethyl cyclohexane.

Preferably, the biocompatible fluid is substantially perfluoroethyldimethyl cyclohexane.

More preferably, the biocompatible fluid is essentially perfluoroethyldimethyl cyclohexane.

Preferably, the biocompatible fluid is administered to an eye as a neat fluid as a vitreous fluid replacement.

Alternatively, the biocompatible fluid is administered to an eye as a carrier for a drug.

Alternatively, the biocompatible fluid is administered to the biological system to provide an $^{19}F$ magnetic resonance spectrum or image of the biological system.

The present invention is also a method of enhancing the oxygen carrying capacity of oxygen through the vascular system and into the tissue of mammals which comprises administering a volumetric amount of a perfluorochemical emulsion to said mammal sufficient to maintain the total vascular volume of said mammal and subjecting the respiratory function of the mammal to elevated concentrations of oxygen above atmospheric concentrations wherein said emulsion comprises perfluoroethyldimethyl cyclohexane, approximately 0.5 up to 7 weight % of a phospholipid which emulsifies said perfluoroethyldimethyl cyclohexane, approximately 5–30 weight % of a triglyceride of fatty acids, and an aqueous medium.

The present invention is further a method of preserving internal organs outside the body which comprises perfusing the same with a preoxygenated perfluoroethyldimethyl cyclohexane emulsion comprising perfluoroethyldimethyl cyclohexane, approximately 0.5 up to 7 weight % of a phospholipid which emulsifies said perfluoroethyldimethyl cyclohexane, approximately 5–30 weight % of a triglyceride of fatty acides and an aqueous media.

Additionally, the present invention is a method of treating hypoxic mammalian tumor cells in vivo in a mammal comprising administering an oxygenated perfluoroethyldimethyl cyclohexane emulsion in a dosage up to the equivalent of 50% of the tumor volume, but less than 2 ml/kg of body weight interstitially directly into the hypoxic zones within said tumor and thereafter subjecting the administered cells to an amount of radiation effective to initiate destruction of said cells.

Finally, the present invention is a method for obtaining a $^{19}F$-fluorine magnetic resonance spectrum or image from body cavities, organs or tissue by administering to a mammal an aqueous isotonic emulsion of perfluoroethyldimethyl cyclohexane-containing agent in a diagnostically effective amount to provide a fluorine magnetic resonance spectrum or image from such cavities, organs or tissues.

DETAILED DESCRIPTION OF THE INVENTION

The new methods of the present invention utilize an agent comprising ethyl dimethyl cyclohexane in a perfluorinated or fully fluorinated condition, which is of interest because the boiling point is comparable to perfluorodecalin, but has physical properties that differ, such as pore point and surface tension. These significantly differing properties from perfluorodecalin provide enhanced utility for such applications as improved transport of biological samples through conduits or tubing because of the low surface tension of the compound of the present invention of 17.4 dynes/cm at 25° C. versus 19.3 dynes/cm at 25° C. for perfluorodecalin. The NMR$^{19}F$ spectrum is 3.0 for $CF_3$, 3.1 for $CF_2$, and 1.0 CF.

The compositions of the present invention constitute essentially single compounds having sharply defined boiling points which do not fractionate off into various components through exposure to cycling from cooldown to high temperature utilization, such utilization as is characteristic of vapor phase soldering fluid unity.

The perfluoroethyldimethyl cyclohexane compound of the present invention which is preferably substituted with methyl at the number 2 and 4 position of the cyclohexane ring has an empirical formula of $C_{10}F_{20}$ and a molecular weight of 500. The material is a liquid at room temperature with a boiling point of approximately 146° C. The general structure of the compound of the present invention has been confirmed by $^{19}F$ NMR (nuclear magnetic resonance spectroscopy) and GC/MS (gas chromatography/mass spectroscopy). Typically, the feedstock to produce such a perfluorinated compound is the hydrocarbon ethyldimethyl cyclohexane or ethyldimethyl benzene, which can be prepared by the alkylation of cyclohexane by known techniques. The present compounds have also been found to be cleavage products of the fluorination process for producing perfluoro-1, 1-di(orthoxylyl) ethane in accordance with U.S. Pat. No. 4,801,761 which is incorporated by reference herein. The new composition of the present invention is substantially a perfluorinated analog of the ethyldimethyl cyclohexane hydrocarbon starting material wherein nearly all aromatic character and hydrogen are removed as a result of the reaction process. All isomers and conformers of ethyldimethyl cyclohexane are represented by the perfluorinated compound of the present invention.

All of these species of the compounds of the present invention have utility for oxygen transport media for in vivo and in vitro use as pure substances or mixtures or emulsions, as well as use as hydraulic fluids, lubricants, heat exchange or cooling fluids and other such applications where chemical inertness and boiling point are the desired physical and chemical properties, most particularly as bio-inert fluids administered to biological systems.

The preparation, identification and emulsification of the compounds of the present invention will be set forth in the following examples.

EXAMPLE 1

In a typical reaction 1,1-di(orthoxylyl)ethane is vaporized to a cobalt trifluoride reactor operating at 230° to 350° C. The resulting fluorochemical product, containing perfluoro-1,1-di(orthoxylyl) methane is collected and separated from hydrogen fluoride by-products. The fluorochemical is distilled to give a spectrum of products. The fluorination process predominantly cleaves the methyl group from the bridging chain between the two ring constituents to change the ethyl bridge to a methylene bridge, but a mixture of the ethyl and methylene bridged compounds are produced which are separated by distillation. Milder fluorination conditions increases the amount of ethyl bridged compound. Cleavage at the bond between the bridge and the ring gives the present compound. Perfluoroethyldimethyl cyclohexane is found as a distillation cut of the fluorination product.

EXAMPLE 2

77 g of 1,1-di(orthoxylyl) ethane was heated to its boiling point in a vaporizer while purging with nitrogen gas. The 1,1-di(orthoxylyl) ethane/nitrogen gas stream was fed to a heated reactor 6" in diameter and 4' long containing approximately 35 lbs. of cobalt trifluoride. The reactor was held at approximately 345° C., in the first half of the reactor and approximately 415° C., in the last half of the reactor. The 1,1-di(orthoxylyl) ethane feed was subsequently converted to 162 g of a perfluorochemical. The crude fluorochemical was filtered to remove any solids and pass thru alumina to remove any active fluorides. A portion of the product distilling at 140°–145° C. is the compound of the present invention.

EXAMPLE 3

143 g of 1,1-di(orthoxylyl) ethane was heated to its boiling point in a vaporizer while purging with nitrogen gas. The 1,1-di(orthoxylyl) ethane/nitrogen gas stream was fed to a heated reactor 6" in diameter and 4' long containing approximately 35 lbs. of cobalt trifluoride. The reactor was held at approximately 345° C., in the first half of the reactor and approximately 415° C., in the last half of the reactor. The 1,1-di(orthoxylyl) ethane feed was subsequently converted to 201 g of a perfluorochemical. The crude fluorochemical was filtered to remove any solids and passed thru alumina to remove any active fluorides.

The compounds can also be synthesized by other fluorination techniques, including direct fluorination with elemental fluorine under mild conditions, as well as fluorination using other fluorine sources than cobalt trifluoride.

EXAMPLE 4

215 g of a crude perfluorochemical prepared in a similar manner to Examples 2 and 3 above was distilled through a glass packed column. A product was collected which had a boiling range of 140°–145° C. Analysis by $^{19}F$ NMR spectroscopy and GC/MS (gas chromatography/mass spectroscopy) confirmed the presence of perfluoroethyldimethyl cyclohexane.

EXAMPLE 5

Perfluoroethyldimethyl cyclohexane (1–100 wt/vol %) can be prepared in isotonic aqueous emulsion using a combination of egg yolk or soy bean lecithin (1–3 wt %); safflower or other triglyceride oil (0.5–2 wt %); and glycerol (0.5–2 wt %), at a pH of 7.0–9.5. The mixture is then subjected to one or more of the following methods: sonication, microfluidization or high pressure (>10,000 psig) homogenization at 20°–45° C. to cause a fine (0.05–0.3 micron) emulsion to occur. The resulting emulsion, pH adjusted as required, may be administered to animals/humans intravenously, intravascularly, subcutaneously, interstitially, intramuscular, intraperitoneal, as fluid lavage, topical, or orally.

The compounds of the present invention also have utility as inert carrier fluids for the testing of biological samples such as blood samples, in automated analysis instruments where individual biological samples are conveyed and/or separated by the perfluoroethyldimethyl cyclohexane as an inert carrier fluid which keeps the samples as discrete portions as the analysis is performed on multiple samples in a continuous process. Additionally, the compounds can be used as transport agents for oxygen in artificial blood, culture media or perfusates for donor organs, where they substitute for existing agents, such as perfluorodecalin and perfluorooctylbromide.

Perfluoroethyldimethyl cyclohexane, a water white liquid with a liquid density of 190 g/cc (25° C.) and vapor pressure of 5 torr at 25° C., can dissolve 49 ml of oxygen and 122 ml of carbon dioxide per 100 ml of net liquid phase. The perfluorochemical fluid can be easily emulsified and remain stable (>60 days) using methods and surfactants as described in U.S. Pat. Nos. 4,866,096 and 4,895,876, hereby incorporated by reference herein in their entirety. This ease of emulsification at concentrations of 5–80 weight/volume (w/v) percent is in contrast to perfluorodecalin, the most recognized oxygen transport fluid for in vivo blood substitutes, whose emulsions are difficult to generate at >20 w/v percent and become unstable unless frozen within three days. Perfluoroethyldimethyl cyclohexane has been shown to produce substantially less insult to the lungs of rabbits (i.e. hyperinflated lung syndrome) when compared to perfluorodecalin. This unexpected result, for a compound boiling at 146° C. is significant and may result because of its unique molecular tumbling radius that allows it to escape from lung tissue.

As a consequence of these unexpected properties, perfluoroethyldimethyl cyclohexane emulsions show exceptional promise as a resuscitative fluid in humans, radiotherapy adjuvant for hypoxic tumor cells (systemic and interstitial) as described in U.S. Pat. No. 4,781,676 which is hereby incorporated by reference herein in its entirety, oxygen adjuvant for angioplasty, organ preservation fluid for transplant, therapeutic lavage for cystic fibrosis, and $^{19}F$ magnetic resonance imaging contrast agent.

Perfluoroethyldimethyl cyclohexane, as a neat perfluorochemical fluid can be used as an ultrasound diagnostic agent because its high density increases the velocity of sound relative to normal tissue (water-based) to improve contrast in the upper and lower gastrointestinal (GI) tract. Perfluoroethyldimethyl cyclohexane can be used to cover or bath second or third degree burns of biological tissue, such as skin, to enhance the healing process by rapid transport of oxygen from the air to the skin while not permitting dehydration and reducing bacterial growth. As a direct consequence of its low toxicity, high gas solubility and unexpectedly low generation of the hyperinflated lung syndrome, perfluoroethyldimethyl cyclohexane can be used as a "liquid breathing agent" in new born infants as an amniotic fluid replacement at 22–26 weeks gestation. Because of perfluoroethyldimethyl cyclohexane's inert qualities to laser (helium, argon, etc.) light intensities, high density, and difference in refractive index relative to water (~1.22 vs. 1.33 for water), it can be used as a vitreous fluid replacement during laser retinal reattachment surgery. The fluid can be easily distinguished as an "oil" during vitreous fluid transfill and subject the retina to a hydrophobic environment for rapid reattachment without excessive movement as a consequence of its density.

Administration of substantially neat perfluoroethyldimethyl cyclohexane can be achieved intraocularly, as a fluid lavage, orally, topical or subcutaneously.

Organs for transplant (human) such as hearts, livers, and lungs are required to be maintained viable for "immediate" functioning in the recipient. To accomplish this today, organs are transplanted within 12–36 hours, depending upon the organ. To extend the storage time and utilize more organs for transplant the subject organ can be suspended in an emulsion (10–30 wt/vol percent) of perfluoroethyldimethyl cyclohexane which contains vital salts. The emulsion is sparged with oxygen and the temperature of the organ/emulsion system cooled to allow long term (24–50 hours) transport/storage prior to transplant. The organ is washed with 2–4 unit volumes of saline to remove the perfluoroethyldimethyl cyclohexane emulsion and used as per the medical protocol or organ transplant.

The use of perfluoroethyldimethyl cyclohexane emulsions (5–30 W,/v percent in broth) with plants, cell cultures or bacterial fermentation will provide enhanced gas transport ($CO_2$ & $O_2$) during a culturing or fermentation process. The culture media is sparged with the appropriate gas ($CO_2$ & $O_2$) allowing for a higher concentration of gas per unit volume of media. As a result of the higher soluble gas concentration one can achieve more viable cells per unit volume of media to improve overall yield.

Emulsion of perfluoroethyldimethyl cyclohexane (20–40 w/v percent) with particle size <0.25 microns (preferably 0.1–0.15 microns) are combined with electrolytes to maintain physiologic pH, ionic strength, and osmotic pressure. This mixture is administered to mammals intravenously via drip to replace blood loss from 10–100%, total blood volume. Perfluoroethyldimethyl cyclohexane is released from the emulsion, gathers in the lung and is lost via respiration within 30–90 days (half-life).

Perfluoroethyldimethyl cyclohexane, as a neat fluid, is sparged with oxygen and pumped into the lungs of a new born infant (22–26 weeks gestation) to act as an amniotic fluid replacement while the lung's native surfactant is developed. The process may involve suspending known surfactants to aid the lung's development process. When the lung has developed the perfluoroethyldimethyl cyclohexane is drained and the infant is permitted to air breathe. Residual perfluoroethyldimethyl cyclohexane is removed via normal respiration.

Emulsions of perfluoroethyldimethyl cyclohexane (20–40 w/v percent) with particle size <0.25 microns (preferably 0.1–0.15 microns) are combined with electrolytes to maintain physiologic pH ionic strength, sparged with oxygen, and as mucus surfactants are washed into the lungs of patients suffering from cystic fibrosis. The action of washing the lung carries the mucus coating out with the lavage to recover the lungs ability to transport oxygen from the air to the blood. This action would act as an adjuvant to the present system of "pounding" on the back of patient (2–4 times) daily to remove the mucus and reduce labored breathing, especially in children.

The compounds of the present invention include perfluoro-1-ethyl-2, 4-dimethyl cyclohexane, perfluoro-1-ethyl-2, 5-dimethyl cyclohexane and perfluoro-1-ethyl-3, 4-dimethyl cyclohexane as the preferred isomers.

The present invention has been set forth with regard to various specific examples and embodiments of the invention. However, the scope of the invention should be ascertained from the claims which follow.

I claim:

1. A method of transporting gases in a fluid system, the improvement comprising using as the gas transport agent a perfluorinated compound having the following structure wherein the ring carbons are fully fluorinated:

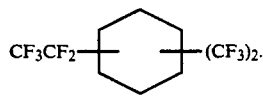

2. The method of claim 1 wherein the compound has the following structure:

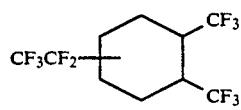

3. The method of claim 1 wherein the compound has the following structure:

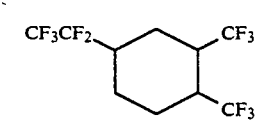

4. The method of claim 1 wherein the compound has the following structure:

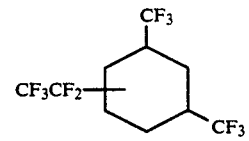

5. The method of claim 1 wherein the compound has the following structure:

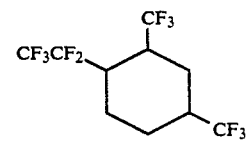

6. The method of claim 1 wherein the compound has the following structure:

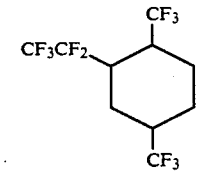

7. The method of claim 1 wherein the gas is oxygen.

8. A method of transporting oxygen gas in a fluid system selected from the group consisting of resusitative blood replacement fluid, radiotherapy fluid for hypoxic tumor therapy, therapeutic fluid for angioplasty, organ preservation fluid for organ transplants, fluid for liquid lung breathing therapy, therapeutic lavage for cystic fibrosis, and cell culture media, using as a gas transport agent a perfluorinated compound of the formula:

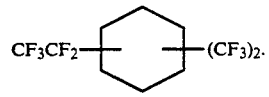

9. The method of claim 8 wherein the perfluorinated compound is in an aqueous emulsion.

10. A method of administering a bio-inert fluid to a biological system, the improvement comprising a biocompatible fluid containing perfluoroethyldimethyl cyclohexane.

11. The method of claim 10 wherein the biocompatible fluid is substantially perfluoroethyldimethyl cyclohexane.

12. The method of claim 10 wherein the biocompatible fluid is essentially perfluoroethyldimethyl cyclohexane.

13. The method of claim 10 wherein the biocompatible fluid is administered to an eye as a neat fluid as a vitreous fluid replacement.

14. The method of claim 10 wherein the biocompatible fluid is administered to an eye as a carrier for a drug.

15. The method of claim 10 wherein the biocompatible fluid is administered to burned biological tissue.

* * * * *